(12) United States Patent
Stocker et al.

(10) Patent No.: US 8,414,641 B2
(45) Date of Patent: *Apr. 9, 2013

(54) VALVE WITH DELAYED LEAFLET DEPLOYMENT

(75) Inventors: Patrick J. Stocker, Ramsey, MN (US); Joseph C. Walker, Shoreview, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/411,049

(22) Filed: Mar. 2, 2012

(65) Prior Publication Data

US 2012/0165927 A1    Jun. 28, 2012

Related U.S. Application Data

(63) Continuation of application No. 13/006,578, filed on Jan. 14, 2011, now Pat. No. 8,137,394, which is a continuation of application No. 12/004,561, filed on Dec. 21, 2007, now Pat. No. 7,892,276.

(51) Int. Cl.
*A61F 2/06* (2006.01)
(52) U.S. Cl. ....................... 623/1.24; 623/2.17
(58) Field of Classification Search ................. 623/1.24, 623/2.11, 2.14
See application file for complete search history.

(56) References Cited

U.S. PATENT DOCUMENTS

| | | | |
|---|---|---|---|
| 3,671,979 A | 6/1972 | Moulopoulos | |
| 4,291,420 A | 9/1981 | Reul | |
| 4,787,901 A | 11/1988 | Baykut | |
| 4,872,874 A | 10/1989 | Taheri | |
| 4,935,030 A | 6/1990 | Alonso | |
| 4,994,077 A | 2/1991 | Dobben | |
| 5,002,567 A | 3/1991 | Bona et al. | |
| 5,141,491 A | 8/1992 | Bowald | |
| 5,163,953 A | 11/1992 | Vince | |
| 5,219,355 A | 6/1993 | Parodi et al. | |
| 5,254,127 A | 10/1993 | Wholey et al. | |
| 5,327,774 A | 7/1994 | Nguyen et al. | |
| 5,332,402 A | 7/1994 | Teitelbaum | |
| 5,370,685 A | 12/1994 | Stevens | |
| 5,411,552 A | 5/1995 | Andersen et al. | |
| 5,469,868 A | 11/1995 | Reger | |
| 5,480,423 A | 1/1996 | Ravenscroft et al. | |
| 5,489,291 A | 2/1996 | Wiley | |

(Continued)

FOREIGN PATENT DOCUMENTS

| | | |
|---|---|---|
| EP | 0380666 | 8/1990 |
| EP | 0466518 | 1/1992 |

(Continued)

*Primary Examiner* — David H Willse
*Assistant Examiner* — Tiffany Shipmon
(74) *Attorney, Agent, or Firm* — Vidas, Arrett & Steinkraus, P.A.

(57) ABSTRACT

A valve for use in a body lumen, where the valve includes a valve leaflet with delayed leaflet deployment relative an in vivo implant time. The valve includes a valve frame, a valve leaflet coupled to the valve frame. The valve leaflet includes a commissure that can reversibly seal for unidirectional flow of a liquid through the valve, and a biodegradable adhesive between the valve leaflet and the valve frame to hold at least the commissure of the valve leaflet in a static relationship relative the valve frame for a predetermined time once implanted in vivo.

20 Claims, 3 Drawing Sheets

U.S. PATENT DOCUMENTS

| | | |
|---|---|---|
| 5,500,014 A | 3/1996 | Quijano et al. |
| 5,545,214 A | 8/1996 | Stevens |
| 5,554,185 A | 9/1996 | Block et al. |
| 5,643,208 A | 7/1997 | Parodi |
| 5,693,087 A | 12/1997 | Parodi |
| 5,713,953 A | 2/1998 | Vallana et al. |
| 5,716,370 A | 2/1998 | Williamson, IV et al. |
| 5,735,859 A | 4/1998 | Fischell et al. |
| 5,741,326 A | 4/1998 | Solovay |
| 5,741,333 A | 4/1998 | Frid |
| 5,800,506 A | 9/1998 | Perouse |
| 5,824,061 A | 10/1998 | Quijano et al. |
| 5,879,320 A | 3/1999 | Cazenave |
| 5,895,419 A | 4/1999 | Tweden et al. |
| 5,910,170 A | 6/1999 | Reimink et al. |
| 6,010,531 A | 1/2000 | Donlon et al. |
| 6,042,607 A | 3/2000 | Williamson, IV et al. |
| 6,139,575 A | 10/2000 | Shu et al. |
| 6,287,334 B1 | 9/2001 | Moll et al. |
| 6,312,447 B1 | 11/2001 | Grimes |
| 6,355,030 B1 | 3/2002 | Aldrich et al. |
| 6,402,780 B2 | 6/2002 | Williamson, IV et al. |
| 6,419,696 B1 | 7/2002 | Ortiz et al. |
| 6,425,916 B1 | 7/2002 | Garrison et al. |
| 6,440,164 B1 | 8/2002 | DiMatteo et al. |
| 6,451,054 B1 | 9/2002 | Stevens |
| 6,454,799 B1 | 9/2002 | Schreck |
| 6,461,366 B1 | 10/2002 | Seguin |
| 6,503,272 B2 | 1/2003 | Duerig et al. |
| 6,508,833 B2 | 1/2003 | Pavcnik et al. |
| 6,564,805 B2 | 5/2003 | Garrison et al. |
| 6,569,196 B1 | 5/2003 | Vesely |
| 6,602,286 B1 | 8/2003 | Strecker |
| 6,629,534 B1 | 10/2003 | St. Goar et al. |
| 6,635,085 B1 | 10/2003 | Caffey et al. |
| 6,666,885 B2 | 12/2003 | Moe |
| 6,666,886 B1 | 12/2003 | Tranquillo et al. |
| 6,669,725 B2 | 12/2003 | Scott |
| 6,673,109 B2 | 1/2004 | Cox |
| 6,676,698 B2 | 1/2004 | McGuckin, Jr. et al. |
| 6,676,702 B2 | 1/2004 | Mathis |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,692,512 B2 | 2/2004 | Jang |
| 6,695,866 B1 | 2/2004 | Kuehn et al. |
| 6,695,878 B2 | 2/2004 | McGuckin, Jr. et al. |
| 6,709,456 B2 | 3/2004 | Langberg et al. |
| 6,709,457 B1 | 3/2004 | Otte et al. |
| 6,716,241 B2 | 4/2004 | Wilder et al. |
| 6,716,244 B2 | 4/2004 | Klaco |
| 6,719,767 B1 | 4/2004 | Kimblad |
| 6,719,784 B2 | 4/2004 | Henderson |
| 6,719,786 B2 | 4/2004 | Ryan et al. |
| 6,719,787 B2 | 4/2004 | Cox |
| 6,719,788 B2 | 4/2004 | Cox |
| 6,719,789 B2 | 4/2004 | Cox |
| 6,719,790 B2 | 4/2004 | Brendzel et al. |
| 6,723,038 B1 | 4/2004 | Schroeder et al. |
| 6,723,122 B2 | 4/2004 | Yang et al. |
| 6,723,123 B1 | 4/2004 | Kazatchkov et al. |
| 6,726,715 B2 | 4/2004 | Sutherland |
| 6,726,716 B2 | 4/2004 | Marquez |
| 6,726,717 B2 | 4/2004 | Alfieri et al. |
| 6,730,118 B2 | 5/2004 | Spenser et al. |
| 6,730,121 B2 | 5/2004 | Ortiz et al. |
| 6,730,122 B1 | 5/2004 | Pan et al. |
| 6,736,845 B2 | 5/2004 | Marquez et al. |
| 6,736,846 B2 | 5/2004 | Cox |
| 6,749,630 B2 | 6/2004 | McCarthy et al. |
| 6,752,813 B2 | 6/2004 | Goldfarb et al. |
| 6,752,828 B2 | 6/2004 | Thornton |
| 6,755,857 B2 | 6/2004 | Peterson et al. |
| 6,761,734 B2 | 7/2004 | Suhr |
| 6,761,735 B2 | 7/2004 | Eberhardt et al. |
| 6,764,494 B2 | 7/2004 | Menz et al. |
| 6,764,508 B1 | 7/2004 | Roehe et al. |
| 6,764,509 B2 | 7/2004 | Chinn et al. |
| 6,764,510 B2 | 7/2004 | Vidlund et al. |
| 6,767,362 B2 | 7/2004 | Schreck |
| 6,769,434 B2 | 8/2004 | Liddicoat et al. |
| 6,770,083 B2 | 8/2004 | Seguin |
| 6,780,200 B2 | 8/2004 | Jansen |
| 6,786,924 B2 | 9/2004 | Ryan et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,231 B2 | 9/2004 | Liddicoat et al. |
| 6,793,673 B2 | 9/2004 | Kowalsky et al. |
| 6,797,000 B2 | 9/2004 | Simpson et al. |
| 6,797,001 B2 | 9/2004 | Mathis et al. |
| 6,797,002 B2 | 9/2004 | Spence et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,810,882 B2 | 11/2004 | Langberg et al. |
| 6,821,297 B2 | 11/2004 | Snyders |
| 6,824,562 B2 | 11/2004 | Mathis et al. |
| 6,830,584 B1 | 12/2004 | Seguin |
| 6,830,585 B1 | 12/2004 | Artof et al. |
| 6,837,902 B2 | 1/2005 | Nguyen et al. |
| 6,840,246 B2 | 1/2005 | Downing |
| 6,840,957 B2 | 1/2005 | DiMatteo et al. |
| 6,846,324 B2 | 1/2005 | Stobie |
| 6,846,325 B2 | 1/2005 | Liddicoat |
| 6,858,039 B2 | 2/2005 | McCarthy |
| 6,869,444 B2 | 3/2005 | Gabbay |
| 6,872,226 B2 | 3/2005 | Cali et al. |
| 6,875,224 B2 | 4/2005 | Grimes |
| 6,875,230 B1 | 4/2005 | Morita et al. |
| 6,875,231 B2 | 4/2005 | Anduiza et al. |
| 6,881,199 B2 | 4/2005 | Wilk et al. |
| 6,881,224 B2 | 4/2005 | Kruse et al. |
| 6,883,522 B2 | 4/2005 | Spence et al. |
| 6,890,352 B1 | 5/2005 | Lentell |
| 6,890,353 B2 | 5/2005 | Cohn et al. |
| 6,893,459 B1 | 5/2005 | Macoviak |
| 6,893,460 B2 | 5/2005 | Spenser et al. |
| 6,896,700 B2 | 5/2005 | Lu et al. |
| 6,902,576 B2 | 6/2005 | Drasler et al. |
| 6,908,478 B2 | 6/2005 | Alferness et al. |
| 6,908,481 B2 | 6/2005 | Cribier |
| 6,911,043 B2 | 6/2005 | Myers et al. |
| 6,913,608 B2 | 7/2005 | Liddicoat et al. |
| 6,916,338 B2 | 7/2005 | Speziali |
| 6,918,917 B1 | 7/2005 | Nguyen et al. |
| 6,921,407 B2 | 7/2005 | Nguyen et al. |
| 6,921,811 B2 | 7/2005 | Zamora et al. |
| 6,926,715 B1 | 8/2005 | Hauck et al. |
| 6,926,730 B1 | 8/2005 | Nguyen et al. |
| 6,929,653 B2 | 8/2005 | Strecter |
| 6,932,838 B2 | 8/2005 | Schwartz et al. |
| 6,936,067 B2 | 8/2005 | Buchanan |
| 6,939,359 B2 | 9/2005 | Tu et al. |
| 6,942,694 B2 | 9/2005 | Liddicoat et al. |
| 6,945,957 B2 | 9/2005 | Freyman |
| 6,945,978 B1 | 9/2005 | Hyde |
| 6,945,996 B2 | 9/2005 | Sedransk |
| 6,945,997 B2 | 9/2005 | Huynh et al. |
| 6,949,122 B2 | 9/2005 | Adams et al. |
| 6,951,571 B1 | 10/2005 | Srivastava |
| 6,951,573 B1 | 10/2005 | Dilling |
| 6,955,689 B2 | 10/2005 | Ryan et al. |
| 6,958,076 B2 | 10/2005 | Acosta et al. |
| 6,962,605 B2 | 11/2005 | Cosgrove et al. |
| 6,964,682 B2 | 11/2005 | Nguyen-Thien-Nhon et al. |
| 6,964,683 B2 | 11/2005 | Kowalsky et al. |
| 6,964,684 B2 | 11/2005 | Ortiz et al. |
| 6,966,925 B2 | 11/2005 | Stobie |
| 6,966,926 B2 | 11/2005 | Mathis |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,976,995 B2 | 12/2005 | Mathis et al. |
| 6,979,350 B2 | 12/2005 | Moll et al. |
| 6,986,775 B2 | 1/2006 | Morales et al. |
| 6,989,027 B2 | 1/2006 | Allen et al. |

| | | |
|---|---|---|
| 6,989,028 B2 | 1/2006 | Lashinski et al. |
| 6,997,950 B2 | 2/2006 | Chawla |
| 6,997,951 B2 | 2/2006 | Solem et al. |
| 7,004,176 B2 | 2/2006 | Lau |
| 7,007,396 B2 | 3/2006 | Rudko et al. |
| 7,011,669 B2 | 3/2006 | Kimblad |
| 7,011,681 B2 | 3/2006 | Vesely |
| 7,011,682 B2 | 3/2006 | Lashinski et al. |
| 7,018,406 B2 | 3/2006 | Seguin et al. |
| 7,018,407 B1 | 3/2006 | Wright et al. |
| 7,018,408 B2 | 3/2006 | Bailey et al. |
| 7,022,134 B1 | 4/2006 | Quijano et al. |
| 7,025,780 B2 | 4/2006 | Gabbay |
| 7,033,390 B2 | 4/2006 | Johnson et al. |
| 7,037,333 B2 | 5/2006 | Myers et al. |
| 7,037,334 B1 | 5/2006 | Hlavka et al. |
| 7,041,128 B2 | 5/2006 | Mcguckin, Jr. et al. |
| 7,041,132 B2 | 5/2006 | Quijano et al. |
| 7,044,966 B2 | 5/2006 | Svanidze et al. |
| 7,044,967 B1 | 5/2006 | Solem et al. |
| 7,048,754 B2 | 5/2006 | Martin et al. |
| 7,048,757 B2 | 5/2006 | Shaknovich |
| 7,052,487 B2 | 5/2006 | Cohn et al. |
| 7,052,507 B2 | 5/2006 | Wakuda et al. |
| 7,063,722 B2 | 6/2006 | Marquez |
| 7,066,954 B2 | 6/2006 | Ryan |
| 7,070,616 B2 | 7/2006 | Majercak et al. |
| 7,077,862 B2 | 7/2006 | Vidlund et al. |
| 7,081,131 B2 | 7/2006 | Thornton |
| 7,087,064 B1 | 8/2006 | Hyde |
| 7,089,051 B2 | 8/2006 | Javerud et al. |
| 7,090,695 B2 | 8/2006 | Solem et al. |
| 2002/0013571 A1 | 1/2002 | Goldfarb et al. |
| 2002/0026216 A1 | 2/2002 | Grimes |
| 2002/0082630 A1 | 6/2002 | Menz et al. |
| 2002/0123802 A1 | 9/2002 | Snyders |
| 2002/0151970 A1 | 10/2002 | Garrison et al. |
| 2002/0183835 A1 | 12/2002 | Taylor et al. |
| 2002/0183838 A1 | 12/2002 | Liddicoat et al. |
| 2002/0198594 A1 | 12/2002 | Schreck |
| 2003/0050694 A1 | 3/2003 | Yang et al. |
| 2003/0130729 A1 | 7/2003 | Paniagua et al. |
| 2003/0163194 A1 | 8/2003 | Quijano et al. |
| 2003/0167071 A1 | 9/2003 | Martin |
| 2003/0171806 A1 | 9/2003 | Mathis et al. |
| 2003/0199975 A1 | 10/2003 | Gabbay |
| 2003/0229394 A1 | 12/2003 | Ogle et al. |
| 2003/0229395 A1 | 12/2003 | Cox |
| 2003/0233142 A1 | 12/2003 | Morales et al. |
| 2003/0236568 A1 | 12/2003 | Hojeibane et al. |
| 2003/0236569 A1 | 12/2003 | Mathis et al. |
| 2004/0002719 A1 | 1/2004 | Oz et al. |
| 2004/0003819 A1 | 1/2004 | St. Goar et al. |
| 2004/0010305 A1 | 1/2004 | Alferness et al. |
| 2004/0015230 A1 | 1/2004 | Moll et al. |
| 2004/0015232 A1 | 1/2004 | Shu et al. |
| 2004/0015233 A1 | 1/2004 | Jansen |
| 2004/0019374 A1 | 1/2004 | Hojeibane et al. |
| 2004/0019377 A1 | 1/2004 | Taylor et al. |
| 2004/0019378 A1 | 1/2004 | Hlavka et al. |
| 2004/0024447 A1 | 2/2004 | Haverich |
| 2004/0024451 A1 | 2/2004 | Johnson et al. |
| 2004/0024452 A1 | 2/2004 | Kruse et al. |
| 2004/0030321 A1 | 2/2004 | Fangrow, Jr. |
| 2004/0030381 A1 | 2/2004 | Shu |
| 2004/0030382 A1 | 2/2004 | St. Goar et al. |
| 2004/0030405 A1 | 2/2004 | Carpentier et al. |
| 2004/0034380 A1 | 2/2004 | Woolfson et al. |
| 2004/0034411 A1 | 2/2004 | Quijano et al. |
| 2004/0039436 A1 | 2/2004 | Spenser et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0044403 A1 | 3/2004 | Bischoff et al. |
| 2004/0049207 A1 | 3/2004 | Goldfarb et al. |
| 2004/0049211 A1 | 3/2004 | Tremulis et al. |
| 2004/0049266 A1 | 3/2004 | Anduiza et al. |
| 2004/0059351 A1 | 3/2004 | Eigler et al. |
| 2004/0059411 A1 | 3/2004 | Strecker |
| 2004/0059412 A1 | 3/2004 | Lytle, IV et al. |
| 2004/0060161 A1 | 4/2004 | Leal et al. |
| 2004/0073301 A1 | 4/2004 | Donlon et al. |
| 2004/0073302 A1 | 4/2004 | Rourke et al. |
| 2004/0078072 A1 | 4/2004 | Tu et al. |
| 2004/0078074 A1 | 4/2004 | Anderson et al. |
| 2004/0082910 A1 | 4/2004 | Constantz et al. |
| 2004/0082923 A1 | 4/2004 | Field |
| 2004/0082991 A1 | 4/2004 | Nguyen et al. |
| 2004/0087975 A1 | 5/2004 | Lucatero et al. |
| 2004/0088045 A1 | 5/2004 | Cox |
| 2004/0088046 A1 | 5/2004 | Speziali |
| 2004/0092858 A1 | 5/2004 | Wilson et al. |
| 2004/0093060 A1 | 5/2004 | Seguin et al. |
| 2004/0093070 A1 | 5/2004 | Hojeibane et al. |
| 2004/0093080 A1 | 5/2004 | Helmus |
| 2004/0097979 A1 | 5/2004 | Svanidze et al. |
| 2004/0098098 A1 | 5/2004 | McGuckin, Jr. et al. |
| 2004/0098112 A1 | 5/2004 | DiMatteo et al. |
| 2004/0102839 A1 | 5/2004 | Cohn et al. |
| 2004/0102840 A1 | 5/2004 | Solem et al. |
| 2004/0102842 A1 | 5/2004 | Jansen |
| 2004/0106976 A1 | 6/2004 | Bailey et al. |
| 2004/0106990 A1 | 6/2004 | Spence et al. |
| 2004/0106991 A1 | 6/2004 | Hopkins et al. |
| 2004/0111096 A1 | 6/2004 | Tu et al. |
| 2004/0117009 A1 | 6/2004 | Cali et al. |
| 2004/0122448 A1 | 6/2004 | Levine |
| 2004/0122512 A1 | 6/2004 | Navia et al. |
| 2004/0122513 A1 | 6/2004 | Navia et al. |
| 2004/0122514 A1 | 6/2004 | Fogarty et al. |
| 2004/0122515 A1 | 6/2004 | Chu |
| 2004/0122516 A1 | 6/2004 | Fogarty et al. |
| 2004/0127979 A1 | 7/2004 | Wilson et al. |
| 2004/0127980 A1 | 7/2004 | Kowalsky et al. |
| 2004/0127981 A1 | 7/2004 | Rahdert et al. |
| 2004/0127982 A1 | 7/2004 | Machold et al. |
| 2004/0133220 A1 | 7/2004 | Lashinski et al. |
| 2004/0133267 A1 | 7/2004 | Lane |
| 2004/0133273 A1 | 7/2004 | Cox |
| 2004/0138742 A1 | 7/2004 | Myers et al. |
| 2004/0138743 A1 | 7/2004 | Myers et al. |
| 2004/0138744 A1 | 7/2004 | Lashinski et al. |
| 2004/0138745 A1 | 7/2004 | Macoviak et al. |
| 2004/0148018 A1 | 7/2004 | Carpentier et al. |
| 2004/0148019 A1 | 7/2004 | Vidlund et al. |
| 2004/0148020 A1 | 7/2004 | Vidlund et al. |
| 2004/0153052 A1 | 8/2004 | Mathis |
| 2004/0153146 A1 | 8/2004 | Lashinski et al. |
| 2004/0153147 A1 | 8/2004 | Mathis |
| 2004/0158321 A1 | 8/2004 | Reuter et al. |
| 2004/0162610 A1 | 8/2004 | Liska et al. |
| 2004/0167539 A1 | 8/2004 | Kuehn et al. |
| 2004/0167620 A1 | 8/2004 | Ortiz et al. |
| 2004/0172046 A1 | 9/2004 | Hlavka et al. |
| 2004/0176839 A1 | 9/2004 | Huynh et al. |
| 2004/0176840 A1 | 9/2004 | Langberg et al. |
| 2004/0181238 A1 | 9/2004 | Zarbatany et al. |
| 2004/0186444 A1 | 9/2004 | Daly et al. |
| 2004/0186558 A1 | 9/2004 | Pavcnik et al. |
| 2004/0186561 A1 | 9/2004 | Mcguckin, Jr. et al. |
| 2004/0186563 A1 | 9/2004 | Lobbi |
| 2004/0186565 A1 | 9/2004 | Schreck |
| 2004/0186566 A1 | 9/2004 | Hindrichs et al. |
| 2004/0193191 A1 | 9/2004 | Starksen et al. |
| 2004/0193253 A1 | 9/2004 | Thorpe et al. |
| 2004/0193260 A1 | 9/2004 | Alferness et al. |
| 2004/0199155 A1 | 10/2004 | Mollenauer |
| 2004/0199183 A1 | 10/2004 | Oz et al. |
| 2004/0199191 A1 | 10/2004 | Schwartz |
| 2004/0204758 A1 | 10/2004 | Eberhardt et al. |
| 2004/0206363 A1 | 10/2004 | Mccarthy et al. |
| 2004/0210240 A1 | 10/2004 | Saint |
| 2004/0210301 A1 | 10/2004 | Obermiller |
| 2004/0210303 A1 | 10/2004 | Sedransk |
| 2004/0210304 A1 | 10/2004 | Seguin et al. |
| 2004/0210305 A1 | 10/2004 | Shu et al. |
| 2004/0210306 A1 | 10/2004 | Quijano et al. |

| | | | | | |
|---|---|---|---|---|---|
| 2004/0210307 A1 | 10/2004 | Khairkhahan | 2005/0075726 A1 | 4/2005 | Svanidze et al. |
| 2004/0215333 A1 | 10/2004 | Duran et al. | 2005/0075729 A1 | 4/2005 | Nguyen et al. |
| 2004/0215339 A1 | 10/2004 | Drasler et al. | 2005/0075730 A1 | 4/2005 | Myers et al. |
| 2004/0220654 A1 | 11/2004 | Mathis et al. | 2005/0075731 A1 | 4/2005 | Artof et al. |
| 2004/0220657 A1 | 11/2004 | Nieminen et al. | 2005/0080483 A1 | 4/2005 | Solem et al. |
| 2004/0225322 A1 | 11/2004 | Garrison et al. | 2005/0085900 A1 | 4/2005 | Case et al. |
| 2004/0225344 A1 | 11/2004 | Hoffa et al. | 2005/0085903 A1 | 4/2005 | Lau |
| 2004/0225348 A1 | 11/2004 | Case et al. | 2005/0085904 A1 | 4/2005 | Lemmon |
| 2004/0225352 A1 | 11/2004 | Osborne et al. | 2005/0090846 A1 | 4/2005 | Pedersen et al. |
| 2004/0225353 A1 | 11/2004 | McGuckin, Jr. et al. | 2005/0096735 A1 | 5/2005 | Hojeibane et al. |
| 2004/0225354 A1 | 11/2004 | Allen et al. | 2005/0096738 A1 | 5/2005 | Cali et al. |
| 2004/0225355 A1 | 11/2004 | Stevens | 2005/0096739 A1 | 5/2005 | Cao |
| 2004/0225356 A1 | 11/2004 | Frater | 2005/0096740 A1 | 5/2005 | Langberg et al. |
| 2004/0230117 A1 | 11/2004 | Tosaya et al. | 2005/0101975 A1 | 5/2005 | Nguyen et al. |
| 2004/0230297 A1 | 11/2004 | Thornton | 2005/0102026 A1 | 5/2005 | Turner et al. |
| 2004/0236411 A1 | 11/2004 | Sarac et al. | 2005/0107810 A1 | 5/2005 | Morales et al. |
| 2004/0236418 A1 | 11/2004 | Stevens | 2005/0107811 A1 | 5/2005 | Starksen et al. |
| 2004/0236419 A1 | 11/2004 | Milo | 2005/0107812 A1 | 5/2005 | Starksen et al. |
| 2004/0243153 A1 | 12/2004 | Liddicoat et al. | 2005/0107872 A1 | 5/2005 | Mensah et al. |
| 2004/0243219 A1 | 12/2004 | Fischer et al. | 2005/0113910 A1 | 5/2005 | Paniagua et al. |
| 2004/0243227 A1 | 12/2004 | Starksen et al. | 2005/0119673 A1 | 6/2005 | Gordon et al. |
| 2004/0243228 A1 | 12/2004 | Kowalsky et al. | 2005/0119734 A1 | 6/2005 | Spence et al. |
| 2004/0243230 A1 | 12/2004 | Navia et al. | 2005/0119735 A1 | 6/2005 | Spence et al. |
| 2004/0254600 A1 | 12/2004 | Zarbatany et al. | 2005/0125011 A1 | 6/2005 | Spence et al. |
| 2004/0254636 A1 | 12/2004 | Flagle et al. | 2005/0131438 A1 | 6/2005 | Cohn |
| 2004/0260276 A1 | 12/2004 | Rudko et al. | 2005/0137449 A1 | 6/2005 | Nieminen et al. |
| 2004/0260317 A1 | 12/2004 | Bloom et al. | 2005/0137450 A1 | 6/2005 | Aronson et al. |
| 2004/0260322 A1 | 12/2004 | Rudko et al. | 2005/0137451 A1 | 6/2005 | Gordon et al. |
| 2004/0260389 A1 | 12/2004 | Case et al. | 2005/0137676 A1 | 6/2005 | Richardson et al. |
| 2004/0260390 A1 | 12/2004 | Sarac et al. | 2005/0137681 A1 | 6/2005 | Shoemaker et al. |
| 2004/0260393 A1 | 12/2004 | Randert et al. | 2005/0137682 A1 | 6/2005 | Justino |
| 2004/0260394 A1 | 12/2004 | Douk et al. | 2005/0137685 A1 | 6/2005 | Nieminen et al. |
| 2004/0267357 A1 | 12/2004 | Allen et al. | 2005/0137686 A1 | 6/2005 | Salahieh et al. |
| 2005/0004583 A1 | 1/2005 | Oz et al. | 2005/0137688 A1 | 6/2005 | Salahieh et al. |
| 2005/0004667 A1 | 1/2005 | Swinford et al. | 2005/0137689 A1 | 6/2005 | Salahieh et al. |
| 2005/0010285 A1 | 1/2005 | Lambrecht et al. | 2005/0137690 A1 | 6/2005 | Salahieh et al. |
| 2005/0010287 A1 | 1/2005 | Macoviak et al. | 2005/0137691 A1 | 6/2005 | Salahieh et al. |
| 2005/0015112 A1 | 1/2005 | Cohn et al. | 2005/0137692 A1 | 6/2005 | Haug et al. |
| 2005/0021056 A1 | 1/2005 | St. Goar et al. | 2005/0137693 A1 | 6/2005 | Haug et al. |
| 2005/0021136 A1 | 1/2005 | Xie et al. | 2005/0137694 A1 | 6/2005 | Haug et al. |
| 2005/0027261 A1 | 2/2005 | Weaver et al. | 2005/0137696 A1 | 6/2005 | Salahieh et al. |
| 2005/0027348 A1 | 2/2005 | Case et al. | 2005/0137697 A1 | 6/2005 | Salahieh et al. |
| 2005/0027351 A1 | 2/2005 | Reuter et al. | 2005/0137698 A1 | 6/2005 | Salahieh et al. |
| 2005/0027353 A1 | 2/2005 | Alferness et al. | 2005/0137699 A1 | 6/2005 | Salahieh et al. |
| 2005/0033398 A1 | 2/2005 | Seguin | 2005/0137700 A1 | 6/2005 | Spence et al. |
| 2005/0033419 A1 | 2/2005 | Alferness et al. | 2005/0137701 A1 | 6/2005 | Salahieh et al. |
| 2005/0033446 A1 | 2/2005 | Deem et al. | 2005/0137702 A1 | 6/2005 | Haug et al. |
| 2005/0038506 A1 | 2/2005 | Webler et al. | 2005/0143807 A1 | 6/2005 | Pavcnik et al. |
| 2005/0038507 A1 | 2/2005 | Alferness et al. | 2005/0143809 A1 | 6/2005 | Salahieh et al. |
| 2005/0043790 A1 | 2/2005 | Seguin | 2005/0143810 A1 | 6/2005 | Dauner et al. |
| 2005/0043792 A1 | 2/2005 | Solem | 2005/0143811 A1 | 6/2005 | Realyvasquez |
| 2005/0049679 A1 | 3/2005 | Taylor et al. | 2005/0149014 A1 | 7/2005 | Hauck et al. |
| 2005/0049692 A1 | 3/2005 | Numamoto et al. | 2005/0149179 A1 | 7/2005 | Mathis et al. |
| 2005/0049696 A1 | 3/2005 | Siess et al. | 2005/0149180 A1 | 7/2005 | Mathis et al. |
| 2005/0049697 A1 | 3/2005 | Sievers | 2005/0149181 A1 | 7/2005 | Eberhardt |
| 2005/0054977 A1 | 3/2005 | Laird et al. | 2005/0159810 A1 | 7/2005 | Filsoufi |
| 2005/0055079 A1 | 3/2005 | Duran | 2005/0159811 A1 | 7/2005 | Lane |
| 2005/0055087 A1 | 3/2005 | Starksen | 2005/0165477 A1 | 7/2005 | Anduiza et al. |
| 2005/0055088 A1 | 3/2005 | Liddicoat et al. | 2005/0165478 A1 | 7/2005 | Song |
| 2005/0055089 A1 | 3/2005 | Macoviak et al. | 2005/0171472 A1 | 8/2005 | Lutter |
| 2005/0060029 A1 | 3/2005 | Le et al. | 2005/0171601 A1 | 8/2005 | Cosgrove et al. |
| 2005/0060030 A1 | 3/2005 | Lashinski et al. | 2005/0177227 A1 | 8/2005 | Heim et al. |
| 2005/0065460 A1 | 3/2005 | Laird | 2005/0177228 A1 | 8/2005 | Solem et al. |
| 2005/0065550 A1 | 3/2005 | Starksen et al. | 2005/0182483 A1 | 8/2005 | Osborne et al. |
| 2005/0065594 A1 | 3/2005 | DiMatteo et al. | 2005/0184122 A1 | 8/2005 | Hlavka et al. |
| 2005/0065597 A1 | 3/2005 | Lansac | 2005/0187614 A1 | 8/2005 | Agnew |
| 2005/0070998 A1 | 3/2005 | Rourke et al. | 2005/0187616 A1 | 8/2005 | Realyvasquez |
| 2005/0075584 A1 | 4/2005 | Cali | 2005/0187617 A1 | 8/2005 | Navia |
| 2005/0075659 A1 | 4/2005 | Realyvasquez et al. | 2005/0192606 A1 | 9/2005 | Paul, Jr. et al. |
| 2005/0075662 A1 | 4/2005 | Pedersen et al. | 2005/0192665 A1 | 9/2005 | Spenser et al. |
| 2005/0075712 A1 | 4/2005 | Biancucci et al. | 2005/0197692 A1 | 9/2005 | Pai et al. |
| 2005/0075713 A1 | 4/2005 | Biancucci et al. | 2005/0197693 A1 | 9/2005 | Pai et al. |
| 2005/0075717 A1 | 4/2005 | Nguyen et al. | 2005/0197694 A1 | 9/2005 | Pai et al. |
| 2005/0075718 A1 | 4/2005 | Nguyen et al. | 2005/0203549 A1 | 9/2005 | Realyvasquez |
| 2005/0075719 A1 | 4/2005 | Bergheim | 2005/0203605 A1 | 9/2005 | Dolan |
| 2005/0075720 A1 | 4/2005 | Nguyen et al. | 2005/0203614 A1 | 9/2005 | Forster et al. |
| 2005/0075723 A1 | 4/2005 | Schroeder et al. | 2005/0203615 A1 | 9/2005 | Forster et al. |
| 2005/0075724 A1 | 4/2005 | Svanidze et al. | 2005/0203616 A1 | 9/2005 | Cribier |
| 2005/0075725 A1 | 4/2005 | Rowe | 2005/0203617 A1 | 9/2005 | Forster et al. |

| | | |
|---|---|---|
| 2005/0203618 A1 | 9/2005 | Sharkawy et al. |
| 2005/0216039 A1 | 9/2005 | Lederman |
| 2005/0216077 A1 | 9/2005 | Mathis et al. |
| 2005/0216078 A1 | 9/2005 | Starksen et al. |
| 2005/0222675 A1 | 10/2005 | Sauter |
| 2005/0222678 A1 | 10/2005 | Lashinski et al. |
| 2005/0228422 A1 | 10/2005 | Machold et al. |
| 2005/0228479 A1 | 10/2005 | Pavcnik et al. |
| 2005/0228486 A1 | 10/2005 | Case et al. |
| 2005/0228494 A1 | 10/2005 | Marquez |
| 2005/0228495 A1 | 10/2005 | Macoviak |
| 2005/0228496 A1 | 10/2005 | Mensah et al. |
| 2005/0234541 A1 | 10/2005 | Hunt et al. |
| 2005/0234546 A1 | 10/2005 | Nugent et al. |
| 2005/0240200 A1 | 10/2005 | Bergheim |
| 2005/0240202 A1 | 10/2005 | Shennib et al. |
| 2005/0240255 A1 | 10/2005 | Schaeffer |
| 2005/0240259 A1 | 10/2005 | Sisken et al. |
| 2005/0240262 A1 | 10/2005 | White |
| 2005/0244460 A1 | 11/2005 | Alferiev et al. |
| 2005/0246013 A1 | 11/2005 | Gabbay |
| 2005/0251251 A1 | 11/2005 | Cribier |
| 2005/0256566 A1 | 11/2005 | Gabbay |
| 2005/0261704 A1 | 11/2005 | Mathis |
| 2005/0261759 A1 | 11/2005 | Lambrecht et al. |
| 2005/0267493 A1 | 12/2005 | Schreck et al. |
| 2005/0267560 A1 | 12/2005 | Bates |
| 2005/0267565 A1 | 12/2005 | Dave et al. |
| 2005/0267571 A1 | 12/2005 | Spence et al. |
| 2005/0267573 A9 | 12/2005 | Macoviak et al. |
| 2005/0267574 A1 | 12/2005 | Cohn et al. |
| 2005/0272969 A1 | 12/2005 | Alferness et al. |
| 2005/0273160 A1 | 12/2005 | Lashinski et al. |
| 2005/0278015 A1 | 12/2005 | Dave et al. |
| 2005/0283178 A1 | 12/2005 | Flagle et al. |
| 2005/0288779 A1 | 12/2005 | Shaoulian et al. |
| 2006/0000715 A1 | 1/2006 | Whitcher et al. |
| 2006/0004439 A1 | 1/2006 | Spenser et al. |
| 2006/0004442 A1 | 1/2006 | Spenser et al. |
| 2006/0009841 A1 | 1/2006 | Mcguckin, Jr. et al. |
| 2006/0009842 A1 | 1/2006 | Huynh et al. |
| 2006/0013805 A1 | 1/2006 | Hebbel et al. |
| 2006/0013855 A1 | 1/2006 | Carpenter et al. |
| 2006/0015136 A1 | 1/2006 | Besselink |
| 2006/0015178 A1 | 1/2006 | Moaddeb et al. |
| 2006/0015179 A1 | 1/2006 | Bulman-Fleming |
| 2006/0020275 A1 | 1/2006 | Goldfarb |
| 2006/0020327 A1 | 1/2006 | Lashinski et al. |
| 2006/0020332 A1 | 1/2006 | Lashinski et al. |
| 2006/0020334 A1 | 1/2006 | Lashinski et al. |
| 2006/0020335 A1 | 1/2006 | Kowalsky et al. |
| 2006/0020336 A1 | 1/2006 | Liddicoat |
| 2006/0025750 A1 | 2/2006 | Starksen et al. |
| 2006/0025784 A1 | 2/2006 | Starksen et al. |
| 2006/0025787 A1 | 2/2006 | Morales et al. |
| 2006/0025854 A1 | 2/2006 | Lashinski et al. |
| 2006/0025855 A1 | 2/2006 | Lashinski et al. |
| 2006/0025856 A1 | 2/2006 | Ryan et al. |
| 2006/0025857 A1 | 2/2006 | Bergheim et al. |
| 2006/0030747 A1 | 2/2006 | Kantrowitz et al. |
| 2006/0030866 A1 | 2/2006 | Schreck |
| 2006/0030882 A1 | 2/2006 | Adams et al. |
| 2006/0030885 A1 | 2/2006 | Hyde |
| 2006/0036317 A1 | 2/2006 | Vidlund et al. |
| 2006/0041305 A1 | 2/2006 | Lauterjung |
| 2006/0041306 A1 | 2/2006 | Vidlund et al. |
| 2006/0047297 A1 | 3/2006 | Case |
| 2006/0047338 A1 | 3/2006 | Jenson |
| 2006/0047343 A1 | 3/2006 | Oviatt et al. |
| 2006/0052804 A1 | 3/2006 | Mialhe |
| 2006/0052867 A1 | 3/2006 | Revuelta et al. |
| 2006/0058817 A1 | 3/2006 | Starksen et al. |
| 2006/0058865 A1 | 3/2006 | Case et al. |
| 2006/0058871 A1 | 3/2006 | Zakay et al. |
| 2006/0058889 A1 | 3/2006 | Case et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0064174 A1 | 3/2006 | Zadno |
| 2006/0069400 A1 | 3/2006 | Burnett et al. |
| 2006/0069430 A9 | 3/2006 | Randert et al. |
| 2006/0074483 A1 | 4/2006 | Schrayer |
| 2006/0074484 A1 | 4/2006 | Huber |
| 2006/0074485 A1 | 4/2006 | Realyvasquez |
| 2006/0085060 A1 | 4/2006 | Campbell |
| 2006/0089708 A1 | 4/2006 | Osse et al. |
| 2006/0095115 A1 | 5/2006 | Bladilah et al. |
| 2006/0095125 A1 | 5/2006 | Chinn et al. |
| 2006/0099326 A1 | 5/2006 | Keogh et al. |
| 2006/0100697 A1 | 5/2006 | Casanova |
| 2006/0100699 A1 | 5/2006 | Vidlund et al. |
| 2006/0106278 A1 | 5/2006 | Machold et al. |
| 2006/0106279 A1 | 5/2006 | Machold et al. |
| 2006/0106456 A9 | 5/2006 | Machold et al. |
| 2006/0111660 A1 | 5/2006 | Wolf et al. |
| 2006/0111773 A1 | 5/2006 | Rittgers et al. |
| 2006/0111774 A1 | 5/2006 | Samkov et al. |
| 2006/0116572 A1 | 6/2006 | Case |
| 2006/0116756 A1 | 6/2006 | Solem et al. |
| 2006/0122686 A1 | 6/2006 | Gilad et al. |
| 2006/0122692 A1 | 6/2006 | Gilad et al. |
| 2006/0122693 A1 | 6/2006 | Biadillah et al. |
| 2006/0127443 A1 | 6/2006 | Helmus |
| 2006/0129235 A1 | 6/2006 | Seguin et al. |
| 2006/0129236 A1 | 6/2006 | Mccarthy |
| 2006/0135476 A1 | 6/2006 | Kutryk et al. |
| 2006/0135964 A1 | 6/2006 | Vesely |
| 2006/0135967 A1 | 6/2006 | Realyvasquez |
| 2006/0136044 A1 | 6/2006 | Osborne |
| 2006/0136045 A1 | 6/2006 | Flagle et al. |
| 2006/0136052 A1 | 6/2006 | Vesely |
| 2006/0136054 A1 | 6/2006 | Berg et al. |
| 2006/0142846 A1 | 6/2006 | Pavcnik et al. |
| 2006/0142847 A1 | 6/2006 | Shaknovich |
| 2006/0142848 A1 | 6/2006 | Gabbay |
| 2006/0142854 A1 | 6/2006 | Alferness et al. |
| 2006/0149358 A1 | 7/2006 | Zilla et al. |
| 2006/0149360 A1 | 7/2006 | Schwammenthal et al. |
| 2006/0149367 A1 | 7/2006 | Sieracki |
| 2006/0149368 A1 | 7/2006 | Spence |
| 2006/0161133 A1 | 7/2006 | Laird et al. |
| 2006/0161248 A1 | 7/2006 | Case et al. |
| 2006/0161250 A1 | 7/2006 | Shaw |
| 2006/0167468 A1 | 7/2006 | Gabbay |
| 2006/0167541 A1 | 7/2006 | Lattouf |
| 2006/0167542 A1 | 7/2006 | Quintessenza |
| 2006/0167543 A1 | 7/2006 | Bailey |
| 2006/0190074 A1 * | 8/2006 | Hill et al. ............ 623/1.23 |
| 2006/0212110 A1 | 9/2006 | Osborne |
| 2006/0246584 A1 * | 11/2006 | Covelli ............ 435/396 |
| 2007/0027535 A1 | 2/2007 | Purdy |

FOREIGN PATENT DOCUMENTS

| | | |
|---|---|---|
| FR | 2728457 | 6/1996 |
| WO | 8800459 | 1/1988 |
| WO | 9015582 | 12/1990 |
| WO | 9501669 | 1/1995 |
| WO | 9619159 | 6/1996 |
| WO | 9803656 | 1/1998 |
| WO | 9846115 | 10/1998 |
| WO | 9904724 | 2/1999 |
| WO | 0067679 | 11/2000 |
| WO | 0115650 | 3/2001 |
| WO | 0117462 | 3/2001 |
| WO | 03047468 | 6/2003 |
| WO | 03084443 | 10/2003 |
| WO | 2004019825 | 3/2004 |
| WO | 2004021893 | 3/2004 |
| WO | 2004023980 | 3/2004 |
| WO | 2004030568 | 4/2004 |
| WO | 2004030569 | 4/2004 |
| WO | 2004030570 | 4/2004 |
| WO | 2004032724 | 4/2004 |
| WO | 2004032796 | 4/2004 |
| WO | 2004037128 | 5/2004 |
| WO | 2004037317 | 5/2004 |
| WO | 2004039432 | 5/2004 |
| WO | 2004043265 | 5/2004 |

| | | | | | |
|---|---|---|---|---|---|
| WO | 2004043273 | 5/2004 | WO | 2005046528 | 5/2005 |
| WO | 2004043293 | 5/2004 | WO | 2005046529 | 5/2005 |
| WO | 2004045370 | 6/2004 | WO | 2005046530 | 5/2005 |
| WO | 2004045378 | 6/2004 | WO | 2005046531 | 5/2005 |
| WO | 2004045463 | 6/2004 | WO | 2005048883 | 6/2005 |
| WO | 2004047677 | 6/2004 | WO | 2005049103 | 6/2005 |
| WO | 2004060217 | 7/2004 | WO | 2005051226 | 6/2005 |
| WO | 2004060470 | 7/2004 | WO | 2005055811 | 6/2005 |
| WO | 2004062725 | 7/2004 | WO | 2005055883 | 6/2005 |
| WO | 2004066803 | 8/2004 | WO | 2005058206 | 6/2005 |
| WO | 2004066826 | 8/2004 | WO | 2005065585 | 7/2005 |
| WO | 2004069287 | 8/2004 | WO | 2005065593 | 7/2005 |
| WO | 2004075789 | 9/2004 | WO | 2005065594 | 7/2005 |
| WO | 2004080352 | 9/2004 | WO | 2005070342 | 8/2005 |
| WO | 2004082523 | 9/2004 | WO | 2005070343 | 8/2005 |
| WO | 2004082527 | 9/2004 | WO | 2005072654 | 8/2005 |
| WO | 2004082528 | 9/2004 | WO | 2005072655 | 8/2005 |
| WO | 2004082536 | 9/2004 | WO | 2005079706 | 9/2005 |
| WO | 2004082537 | 9/2004 | WO | 2005082288 | 9/2005 |
| WO | 2004082538 | 9/2004 | WO | 2005082289 | 9/2005 |
| WO | 2004082757 | 9/2004 | WO | 2005084595 | 9/2005 |
| WO | 2004084746 | 10/2004 | WO | 2005087139 | 9/2005 |
| WO | 2004084770 | 10/2004 | WO | 2005087140 | 9/2005 |
| WO | 2004089246 | 10/2004 | WO | 2006000763 | 1/2006 |
| WO | 2004089250 | 10/2004 | WO | 2006000776 | 1/2006 |
| WO | 2004089253 | 10/2004 | WO | 2006002492 | 1/2006 |
| WO | 2004091449 | 10/2004 | WO | 2006004679 | 1/2006 |
| WO | 2004091454 | 10/2004 | WO | 2006005015 | 1/2006 |
| WO | 2004093638 | 11/2004 | WO | 2006009690 | 1/2006 |
| WO | 2004093726 | 11/2004 | WO | 2006011127 | 2/2006 |
| WO | 2004093728 | 11/2004 | WO | 2006012011 | 2/2006 |
| WO | 2004093730 | 11/2004 | WO | 2006012013 | 2/2006 |
| WO | 2004093745 | 11/2004 | WO | 2006012038 | 2/2006 |
| WO | 2004093935 | 11/2004 | WO | 2006012068 | 2/2006 |
| WO | 2004096100 | 11/2004 | WO | 2006012322 | 2/2006 |
| WO | 2004103222 | 12/2004 | WO | 2006019498 | 2/2006 |
| WO | 2004103223 | 12/2004 | WO | 2006026371 | 3/2006 |
| WO | 2004105584 | 12/2004 | WO | 2006026377 | 3/2006 |
| WO | 2004105651 | 12/2004 | WO | 2006026912 | 3/2006 |
| WO | 2004112582 | 12/2004 | WO | 2006027499 | 3/2006 |
| WO | 2004112585 | 12/2004 | WO | 2006028821 | 3/2006 |
| WO | 2004112643 | 12/2004 | WO | 2006029062 | 3/2006 |
| WO | 2004112652 | 12/2004 | WO | 2006031436 | 3/2006 |
| WO | 2004112657 | 12/2004 | WO | 2006031469 | 3/2006 |
| WO | 2004112658 | 12/2004 | WO | 2006032051 | 3/2006 |
| WO | 2005000152 | 1/2005 | WO | 2006034245 | 3/2006 |
| WO | 2005002424 | 1/2005 | WO | 2006035415 | 4/2006 |
| WO | 2005002466 | 1/2005 | WO | 2006041505 | 4/2006 |
| WO | 2005004753 | 1/2005 | WO | 2006044679 | 4/2006 |
| WO | 2005007017 | 1/2005 | WO | 2006048664 | 5/2006 |
| WO | 2005007018 | 1/2005 | WO | 2006050459 | 5/2006 |
| WO | 2005007036 | 1/2005 | WO | 2006050460 | 5/2006 |
| WO | 2005007037 | 1/2005 | WO | 2006054107 | 5/2006 |
| WO | 2005009285 | 2/2005 | WO | 2006054930 | 5/2006 |
| WO | 2005009286 | 2/2005 | WO | 2006055982 | 5/2006 |
| WO | 2005009505 | 2/2005 | WO | 2006060546 | 6/2006 |
| WO | 2005009506 | 2/2005 | WO | 2006063108 | 6/2006 |
| WO | 2005011473 | 2/2005 | WO | 2006063181 | 6/2006 |
| WO | 2005011534 | 2/2005 | WO | 2006063199 | 6/2006 |
| WO | 2005011535 | 2/2005 | WO | 2006064490 | 6/2006 |
| WO | 2005013860 | 2/2005 | WO | 2006065212 | 6/2006 |
| WO | 2005018507 | 3/2005 | WO | 2006065930 | 6/2006 |
| WO | 2005021063 | 3/2005 | WO | 2006066148 | 6/2006 |
| WO | 2005023155 | 3/2005 | WO | 2006066150 | 6/2006 |
| WO | 2005025644 | 3/2005 | WO | 2006069094 | 6/2006 |
| WO | 2005027790 | 3/2005 | WO | 2006070372 | 7/2006 |
| WO | 2005027797 | 3/2005 | WO | 2006073628 | 7/2006 |
| WO | 2005034812 | 4/2005 | WO | 2006076890 | 7/2006 |
| WO | 2005039428 | 5/2005 | | | |
| WO | 2005039452 | 5/2005 | | | |
| WO | 2005046488 | 5/2005 | * cited by examiner | | |

VALVE WITH DELAYED LEAFLET DEPLOYMENT

CROSS-REFERENCE TO RELATED APPLICATIONS

This application is a continuation of U.S. patent application Ser. No. 13/006,578, filed Jan. 14, 2011, which is a continuation of U.S. patent application Ser. No. 12/004,561, filed Dec. 21, 2007, each of which are herein incorporated by reference in their entirety.

TECHNICAL FIELD

The present disclosure relates generally to a valve for use in a body lumen, and more particularly to a valve having a valve leaflet with delayed leaflet deployment relative an in vivo implant time.

BACKGROUND

Heart failure is rapidly becoming one of the most common cardiovascular disorders. Unfortunately, an optimal treatment for heart failure has not yet been determined.

Generally, heart failure is classified as a syndrome which develops as a consequence of cardiac disease, and is recognized clinically by different signs and symptoms that are produced by complex circulatory and neuro-hormonal responses to cardiac dysfunction.

Dysfunction in one or both of the systolic function and/or the diastolic function of the heart can lead to heart failure. For example, left ventricular diastolic dysfunction is recognized as a condition leading to morbidity, hospitalizations and death. Left ventricular diastolic dysfunction is a condition in which the left ventricle of the heart exhibits a decreased functionality. This decreased function could lead to congestive heart failure or myocardial infarction, among other cardiovascular diseases.

Treatment of left ventricular diastolic dysfunction can include the use of pharmaceuticals. Despite these treatments, improving the approach to treating diastolic dysfunction continues to be a goal of the medical community.

DETAILED DESCRIPTION

Figure 1:
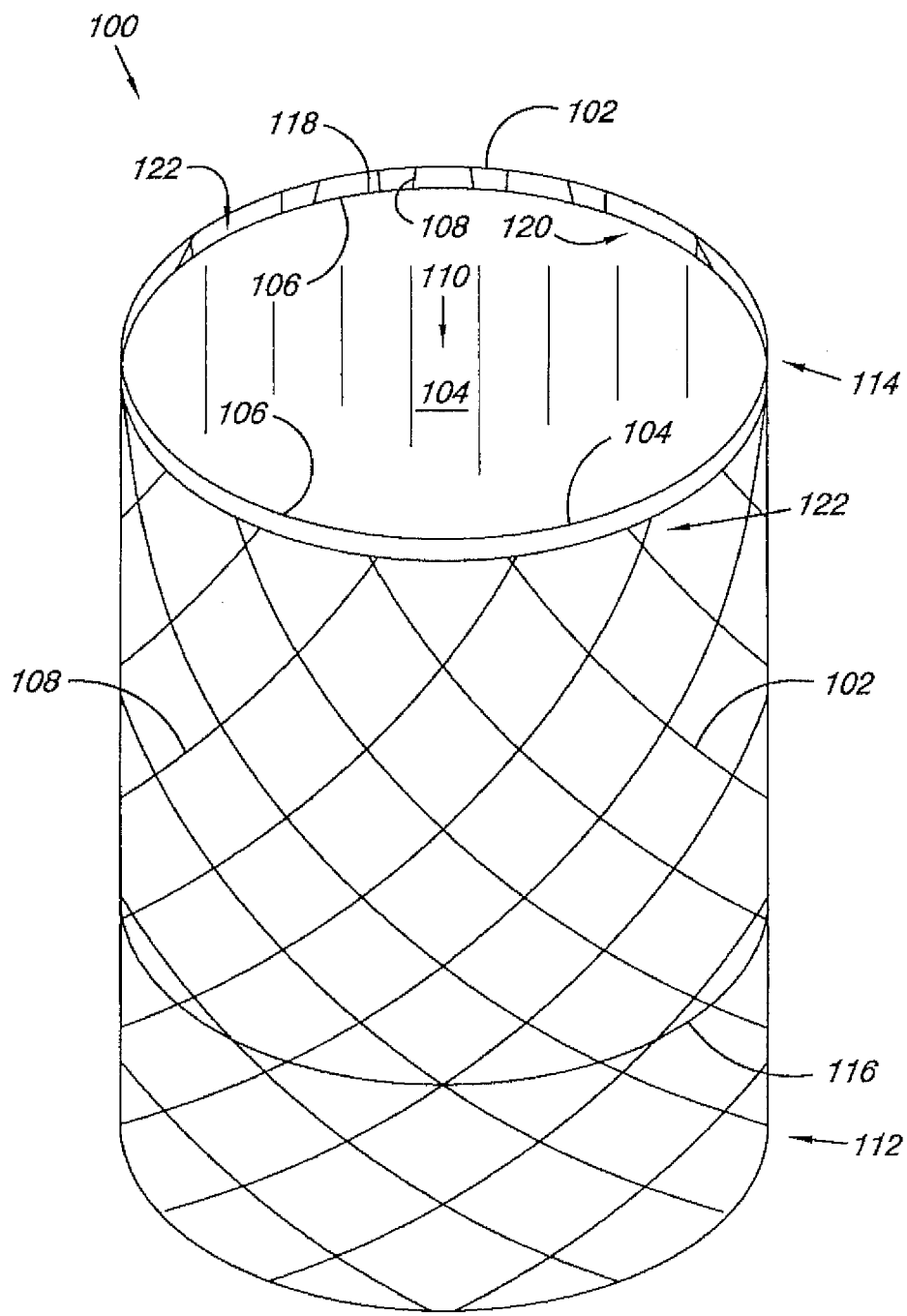
FIG. 1 illustrates an embodiment of a valve of the present disclosure.

Embodiments of the present disclosure are directed to a valve having a valve leaflet, a system that includes the valve, and a method of making and/or using the valve. For the embodiments, the valve leaflet has a delayed deployment relative an in vivo implant time of the valve. For the embodiments, the delayed deployment can be accomplished through the use of a biodegradable adhesive (e.g., a biodegradable material) that holds the valve leaflet in a static relationship relative the valve frame for a predetermined time. Once implanted in vivo, the biodegradable adhesive degrades and/or erodes over the predetermined time to at least the point where the valve leaflet is released from its static relationship relative the valve frame. Once released, the valve leaflet can then operate to control the flow of a fluid through the valve in an essentially unidirectional manner.

As used herein, the terms "a," "an," "the," "one or more," and "at least one" are used interchangeably and include plural referents unless the context clearly dictates otherwise. Unless defined otherwise, all scientific and technical terms are understood to have the same meaning as commonly used in the art to which they pertain. For the purpose of the present disclosure, additional specific terms are defined throughout.

As used herein, the "valve" can be formed from a number of metals, metal alloys, biological materials and/or synthetic materials. For example, the valve leaflet can be formed from one or more of a biological material (e.g., a non-autologous material) and/or a synthetic material (e.g., a synthetic polymer) having suitable mechanical and material properties. In addition, the valve frame can be formed from a synthetic material, a metal and/or a metal alloy having suitable mechanical and material properties. Other materials are also possible. The materials used in forming the valve will be discussed more fully herein.

The valve of the present disclosure can be implanted in one or more vessels of a mammal (e.g., a human) body where it would be desirable to allow the valve frame to first seat (e.g., anchor) and be at least be partially in-grown at the implant site before exposing the valve to forces imparted through the opening and closing of the valve leaflet. For the various embodiments, the valve leaflets maintain their "open" configuration (i.e., their static relationship relative the valve frame) through the use of the biodegradable adhesive, as discussed herein. In this "open" configuration longitudinal shear stresses through the valve can be minimized, allowing the valve frame to seat and be in-grown at the implant site over the predetermined time.

As used herein, the one or more "vessels" can include vessels of the cardiovascular system (e.g., arteries and veins), which can include both the coronary and/or the peripheral vasculature, vessels of the lymphatic system, vessels and/or ducts of the urinary system, and/or vessels and/or ducts of the kidney system. Other vessel locations within the mammal body for implanting the valve of the present disclosure are also possible.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide any number of additional embodiments of valve and/or system. In addition, as will be appreciated the proportion and the relative scale of the elements provided in the figures are intended to illustrate the embodiments of the present disclosure, and should not be taken in a limiting sense.

Various non-limiting embodiments of the present disclosure are illustrated in the figures. Generally, the valve can be implanted within a vessel to regulate the flow of a bodily fluid through the body lumen in a single direction.

FIG. 1 provides an embodiment of a valve 100 that includes a valve frame 102 and a valve leaflet 104 coupled to the valve frame 102. As illustrated, the valve 100 can be formed with a valve leaflet 104 having a commissure 106 that can reversibly seal for unidirectional flow of a liquid through the valve 100. As discussed herein, embodiments of the valve 100 having one leaflet 104 or more than two leaflets 104 are possible.

The valve frame 102 also includes frame members 108 that help to define a lumen 110. For the various embodiments, the valve frame 102 can have an elongate tubular structure with a proximal end 112 and a distal end 114. For the various embodiments, portions of the frame members 108 define the proximal and distal ends 112, 114 of the valve frame 102.

The valve leaflet 104 also has a proximal end 116 and a distal end 118. As illustrated, the proximal end 116 of the leaflet 104 can be coupled to the valve frame 102 through a number of different techniques. For example, the material 120 forming the leaflet 104 can be stitched, bonded, glued or otherwise secured to the valve frame 102 so as to form the proximal end 116 of the valve leaflet 104. In one embodiment, the material 120 can be secured to the valve frame 102 at a position that is at or adjacent the proximal end 112. Alternatively, the material 120 can be secured to the valve frame 102 at a position that is between the proximal and distal ends 112, 114 of the valve frame 102. For the various embodiments, the material 120 forming the valve leaflet 104 can define at least a part of the lumen 110 of the valve 100.

As illustrated, the distal end 118 of the valve leaflet 104 includes the commissure 106 that can reversibly form to control fluid flow through the valve 100. As used herein, the commissure 106 is the location of the valve leaflet 104 that releasably join and seal to allow for unidirectional flow through the valve 100. As illustrated, the commissure 106 is approximately adjacent the distal end 118 of the valve leaflet 104.

As illustrated, the valve leaflet 104 is in an open position. For the various embodiments, the valve leaflet 104 can releasably joined to be held in this open position with a biodegradable adhesive 122 so that the commissure 106 does not help to prevent retrograde flow for at least a predetermined time after the valve has been implanted in a vessel of a body. As used herein, a "biodegradable adhesive" includes those materials that when exposed to a biological environment (e.g., in vivo) is chemically and/or physically degraded via one or more mechanisms. These mechanisms can include, but are not limited to, hydrolysis and/or enzymatic cleavage of the biodegradable material (e.g., scission of the polymer backbone).

With respect to valve 100, the biodegradable adhesive 122 can be positioned between the valve leaflet 104 and the valve frame 102 to hold at least the commissure 106 of the valve leaflet 104 in a static relationship relative the valve frame 102. For the various embodiments, the biodegradable adhesive 122 can originally be in the form of a liquid and/or a solid (including a gel) that can be used to join valve leaflet 104 to the valve frame 102. For example, the biodegradable adhesive 122 can be applied to one or both adjacent surfaces of the valve leaflet 104 and the valve frame 102, where the surfaces are brought together to join them with the biodegradable adhesive 122. Other forms for the biodegradable adhesive 122 are also possible.

For the various embodiments, the location(s) of and/or the surface area used with the biodegradable adhesive 122 to hold the valve leaflet 104 in the open position can vary from the proximal end 116 to the distal end 118 (or visa versa) and/or radially around the valve 100. For example, the biodegradable adhesive 122 can be positioned so as to hold the valve leaflet 104 at one or more discrete attachment points between the leaflet 104 and the frame 102. In an additional example, the biodegradable adhesive 122 can be positioned so as to hold at least the valve leaflet 104 completely along the distal end 114 of the valve frame 102. In other words, the biodegradable adhesive 122 can releasably join at least a portion of the valve leaflet 104 to the valve frame 102 along a peripheral edge of the valve leaflet 104 to the valve frame 102. For the various embodiments, releasably joining the portion of the peripheral edge of the valve leaflet 104 to the valve frame 102 includes releasably joining the peripheral edge in its entirety to the valve frame 102. Alternatively, releasably joining the portion of the peripheral edge of the valve leaflet 104 to the valve frame 102 can be at attachment points spaced equidistant from a longitudinally axis of the valve frame 102. For these embodiments, the biodegradable adhesive 122 can hold at least the commissure 106 of the valve leaflet 104 in the static relationship relative the valve frame 102 for the predetermined time after implantation into a lumen of a body.

For the various embodiments, the biodegradable adhesive 122 can be positioned between an outer surface (opposite the luminal surface) of the valve leaflet 104 and the frame member 108. In addition, the biodegradable adhesive 122 can be located over essentially the entire outer surface of the valve leaflet 104 so as to allow the biodegradable adhesive 122 to span the openings defined by the frame member 108.

For the various embodiments, the concentration(s), type, and/or mixture (e.g., two or more different biodegradable adhesives along with other optional substances) of the biodegradable adhesive 122 being used to hold the valve leaflet 104 in the open position can be varied as well. As use herein, the term "concentration" includes the amount of each of the biodegradable adhesives (e.g., by weight) in the mixture and/or solution forming the adhesive.

For the various embodiments, the selection of one or more biodegradable adhesives, their concentration and/or their location used in holding the valve leaflet 104 static relative the valve frame 102 can allow the valve leaflet 104 to release from the valve frame in a number of ways. For example, the biodegradable adhesives 122 can be used in such a way as to allow for a progressive release of the valve leaflet 104 from one of the proximal end 112 and/or the distal end 114 of the valve frame 102. In one approach, this might be accomplished by changing the concentration and/or having a gradient of the biodegradable adhesive(s) 122 that extends from the one or both of either the proximal end 112 and/or the distal end 114 of the valve frame 102.

Alternatively, the selection of one or more biodegradable adhesives 122, their concentration and/or their location can be used in such a way as to allow for each of the valve leaflets 104 to be release from their static relationship in essentially their entirety at essentially the same time. For example, different types of the biodegradable adhesives 122 can be used in different regions (e.g., discrete regions) so as to allow for the progressive release of the valve leaflet 104.

For the various embodiments, the type of biodegradable adhesives can include, but are not limited to those compounds that erode (e.g., bioerodible or biodegradable) so as to be absorbed by the body. As used herein, "erode" or "erosion" includes processes by which a material that is insoluble in water is converted into one that is water-soluble. Other types of biodegradable adhesives can include a variety of natural, synthetic, and biosynthetic polymers that are biodegradable, such as those having at least a heteroatom-containing polymer backbone. Such biodegradable adhesives can include those having chemical linkages such as anhydride, ester, or amide bonds, among others. These chemical linkages can then undergo degradation through one or both of hydrolysis and/or enzymatic cleavage resulting in a scission of the polymer backbone.

Examples of biodegradable adhesives 122 are those that include poly(esters) based on polylactide (PLA), polyglycolide (PGA), polycaprolactone (PCL), and copolymers thereof. Other biodegradable adhesives 122 can include those that having poly(hydroxyalkanoate)s of the PHB-PHV class, additional poly(ester)s, and natural polymers, such as modified poly(saccharide)s, e.g., starch, cellulose, and chitosan, which upon further hydrolysis can yield low molecular weight oligosaccharides. Poly(ethylene oxide), PEO, and/or poly(ethylene glycol), PEG, can also be used as the biodegradable adhesive. Multiblock copolymers of poly(ethylene oxide) (PEO) and poly(butylene terephthalate) (PBT) are also possible for use in the biodegradable adhesives of the present disclosure, where the degradation rate can be influenced by PEO molecular weight and content.

For the various embodiments, the biodegradable adhesive 122 can hold at least the commissure 106 of the valve leaflet 104 in the static relationship relative the valve frame 102 for a predetermined time after implantation into a lumen of a body. For the various embodiments, the predetermined time after implantation can be a range of approximate time, as the degradation of the biodegradable adhesive 122 will most likely proceed at a different rate for each individual patient. As such, the type(s), concentration(s), and/or location(s) of the biodegradable adhesive 122 used in any particular valve 100 may be patient specific and/or implant location specific.

For example, the biodegradable adhesive 122 can hold at least a portion of the valve leaflet 104 static relative the valve frame 102 for no less than one week (i.e., 7 days). After this predetermined time the biodegradable adhesive 122 can have degraded and/or eroded to a point that the biodegradable adhesive 122 no longer can hold the at least a portion of the valve leaflet 104 static relative the valve frame 102. The valve leaflet 104 can then be released from the portions of the valve frame 102 with the biodegradable adhesive 122. After being released, the valve leaflet 104 can then operate to control the flow of a fluid (e.g., blood) through the valve in an essentially unidirectional manner.

For the various embodiments, the predetermined time also allows the valve frame 102 to be at least be partially in-grown at the implant site (e.g., anchor) before exposing the valve 100 to forces imparted through the opening and closing of the valve leaflet 104. In one embodiment, the valve frame 102 can have one or more of a surface treatment and/or a coating that promotes and/or discourages in-growth and/or overgrowth of the surrounding tissues. For example, the valve frame 102 can have one or more of the surface treatment and/or the coating that promotes tissue in-growth in regions of the valve 100 where the valve leaflet 104 was not attached to the valve frame 102 with the biodegradable adhesive 122. Similarly, the regions where the biodegradable adhesive 122 joints the valve leaflet 104 and the valve frame 102 can include one or more of the surface treatment and/or the coating that discourages in-growth and/or overgrowth of the surrounding tissues at least for the time it takes for the biodegradable adhesive 122 to degrade and/or erode.

For the various embodiments, the biodegradable adhesive 122 and/or the valve frame 102 can also have a predetermined structure and/or shape that allows for tissue in-growth of the valve 100, while preventing in-growth around the valve leaflet 104 while it is in its static relationship to the valve frame 102. For example, the biodegradable adhesive 122 positioned between the valve leaflet 104 and the valve frame 102 can have a portion or a layer with a porosity that promotes and/or allows for tissue in-growth, while an adjacent portion of the biodegradable adhesive 122 may not be designed to promote such in-growth. In other words, the biodegradable adhesive 122 can have a layered structure in which the different layers and/or regions can potentially promote different in-growth responses from the body due the physical structure and/or morphology of the biodegradable adhesive 122. Alternatively, different types of biodegradable adhesives 122 can be used in either layers and/or patterns having the same and/or different morphology (e.g., structure such as porous) in trying to elicit the in-growth response discussed herein.

In some embodiments, the frame members 108 of the valve frame 102 can be formed of a variety of materials. Such materials include, but are not limited to, metals, metal alloys, and/or polymers. The design and configuration of the valve frame 102 can be such that it is balloon expandable, either fully or at least partially, and/or self expanding shape-memory materials. Examples of shape-memory materials include shape memory plastics, polymers, thermoplastic materials, and metal-alloys which are inert in the body. Some shape-memory materials, (e.g., nickel-titanium alloys) can be temperature-sensitive and change shape at a designated temperature or temperature range. In one embodiment, the shape memory metal-alloy includes those made from nickel and titanium in specific ratios, commonly known as Nitinol. Other materials are also possible.

For the various embodiments, the frame members 102 can have similar and/or different cross-sectional geometries along their length. The similarity and/or the differences in the cross-sectional geometries can be selected based on one or more desired functions to be elicited from each portion of the valve frame 102. Examples of cross-sectional geometries include rectangular, non-planar configuration (e.g., bent), round (e.g., circular, oval, and/or elliptical), polygonal, arced, and tubular. Other cross-sectional geometries are possible.

The valve 100 can further include one or more radiopaque markers (e.g., tabs, sleeves, welds). For example, one or more portions of the valve frame 102 can be formed from a radiopaque material. Radiopaque markers can be attached to and/or coated onto one or more locations along the valve frame 102. Examples of radiopaque material include, but are not limited to, gold, tantalum, and platinum. The position of the one or more radiopaque markers can be selected so as to provide information on the position, location, and orientation of the valve 100 during its implantation.

The valve 100 further includes the valve leaflets 104 having surfaces defining a reversibly sealable opening (e.g., the commissure 106) for unidirectional flow of a liquid through the valve 100. Each of the valve leaflets 104 are coupled to the valve frame 102, where the leaflets 104 can repeatedly move between an open state and a closed state for unidirectional flow of a liquid through a lumen of the valve 100 after the biodegradable adhesive 122 has degraded and/or eroded to the point where the valve leaflets 104 are released from their static relationship with the valve frame 102. In the present example, the valve 100 includes two of the valve leaflets 104 for a bi-leaflet configuration. As appreciated, mono-leaflet, tri-leaflet and/or other multi-leaflet configurations are also possible.

In some embodiments, the leaflets 104 can be derived from autologous, allogeneic or xenograft material. As will be appreciated, sources for xenograft material (e.g., cardiac valves) include, but are not limited to, mammalian sources such as porcine, equine, and sheep. Additional biologic materials from which to form the valve leaflets 104 include, but are not limited to, explanted veins, pericardium, facia lata, harvested cardiac valves, bladder, vein wall, various collagen types, elastin, intestinal submucosa, and decellularized basement membrane materials, such as small intestine submucosa (SIS), amniotic tissue, or umbilical vein.

Alternatively, the leaflets 104 can be formed from a synthetic material. Possible synthetic materials include, but are not limited to, expanded polytetrafluoroethylene (ePTFE), polytetrafluoroethylene (PTFE), polystyrene-polyisobutylene-polystyrene (SIBS), polyurethane, segmented poly(carbonate-urethane), polyester, polyethylene (PE), polyethylene terephthalate (PET), silk, urethane, Rayon, Silicone, or the like. In an additional embodiment, the synthetic material can also include metals, such as stainless steel (e.g., 316L) and Nitinol. These synthetic materials can be in a woven, a knit, a cast or other known physical fluid-impermeable or permeable configurations. In addition, gold plated metals can be embedded in the leaflet 104 material (e.g., a sandwich configuration) to allow for visualization of the leaflets 104 post placement.

As will be appreciated, the valve 100 (e.g., valve frame 102 and/or valve leaflets 104) can be treated and/or coated with any number of surface or material treatments. Examples of such treatments include, but are not limited to, bioactive agents, including those that modulate thrombosis, those that encourage cellular in-growth, through-growth, and endothelialization, those that resist infection, anti-thromobogenic coatings, and those that reduce calcification. One example of a suitable coating for at least the valve frame 102 is a stent frame coating provided under the trade designator Taxus® from Boston Scientific.

Figure 2A:
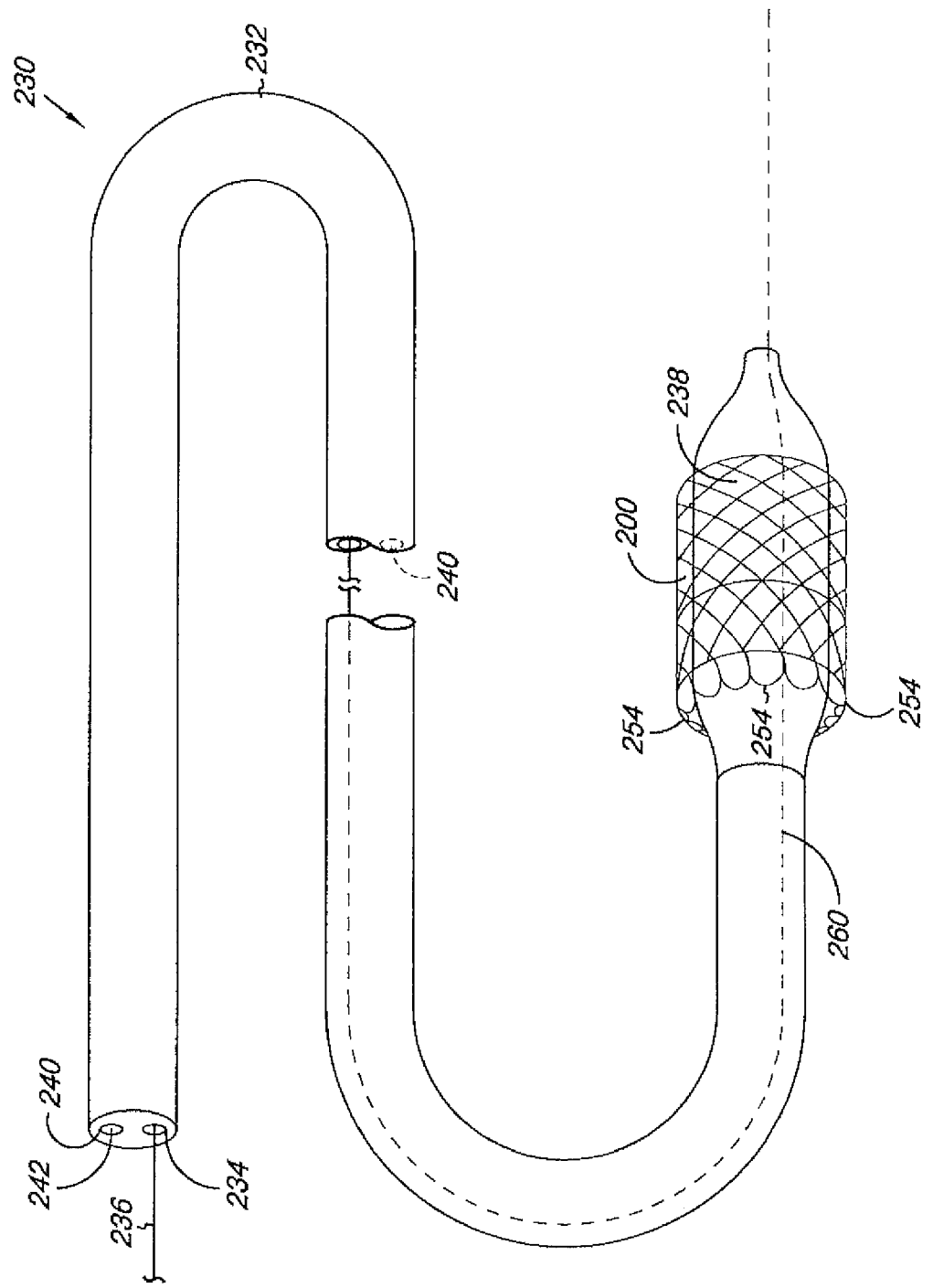
FIG. 2A illustrates an embodiment of a system having a valve of the present disclosure.
Figure 2B:
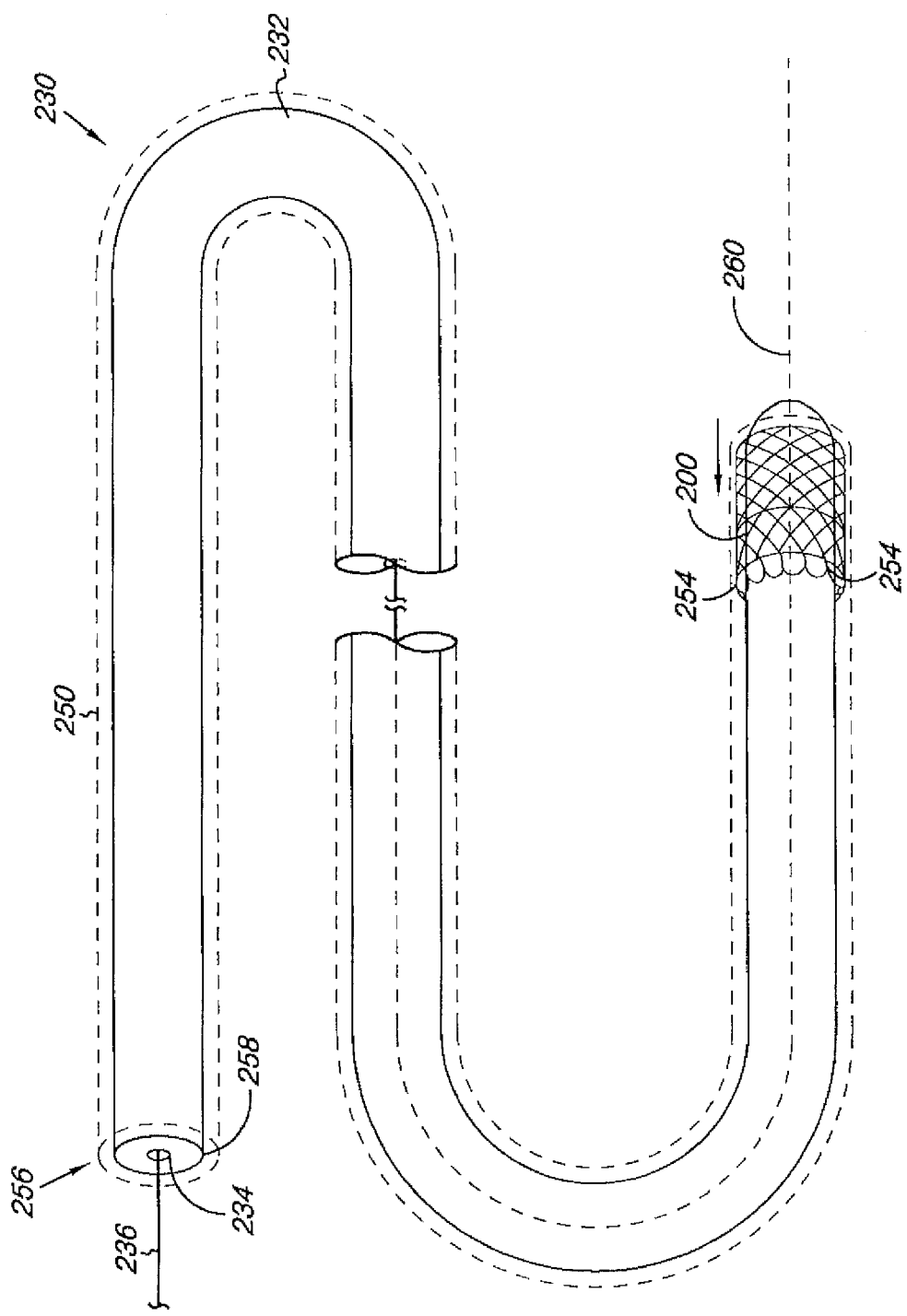
FIG. 2B illustrates an embodiment of a system having a valve of the present disclosure.

Referring now to FIGS. 2A-2B, there is illustrated different embodiments of a system 230 according to the present disclosure. For each system 230, there is at least a valve 200, as described herein, positioned at least partially over an elongate delivery catheter 232. As illustrated, the elongate delivery catheter 232 can include a guide wire lumen 234 for receiving and passing a guide wire 236.

The embodiment of the system 230 illustrated in FIG. 2A further includes an expandable balloon 238 positioned around at least a portion of the elongate delivery catheter 232, and where the valve 200 is positioned at least partially over the expandable balloon 238. For this embodiment, the elongate delivery catheter 232 further includes an inflation lumen 240 that extends through the elongate delivery catheter 232 from an inflation port 242 to an expandable volume defined at least in part by the expandable balloon 238 and the elongate delivery catheter 232. Fluid delivered under pressure through the inflation port 242 can then be used to inflate the expandable balloon 238 thereby at least partially, or completely, delivering the valve 200 to the desired location.

In some embodiments, the expandable balloon 238 can be a perfusion balloon. A perfusion balloon can be used to radially expand the valve frame of the valve 200 while allowing fluid, for example, blood, to pass through the delivery catheter 232 and valve 200 while the valve 200 is being positioned in the vasculature.

In an alternative embodiment, FIG. 2B provides an illustration of a system 230 that includes a retractable sheath 250 positioned around at least a portion of the elongate delivery catheter 232. In addition, at least a portion of the valve 200 can be positioned between the elongate delivery catheter 232 and the retractable sheath 250 to hold the valve 200 in a delivery state. For example, FIG. 2B illustrates an embodiment in which the retractable sheath 250 is positioned around at least a portion of the delivery catheter 232 to releasably hold the valve 200 in its compressed delivery (i.e., undelivered) state. The retractable sheath 250 can be retracted to allow the valve 200 to radially expand from the elongate delivery catheter 232, where the valve frame 202 is formed at least partially from a shape memory material such as Nitinol.

Alternatively, the valve frame 202 can be formed of a material with a spring bias, where the valve 200 can expand when the sheath 250 has been removed. Examples of materials with a spring bias can include, but are not limited to, medical grade stainless steel (e.g., 316L), titanium, tantalum, platinum alloys, niobium alloys, cobalt alloys, alginate, or combinations thereof.

In one embodiment, the retractable sheath 250 can extend co-axially with the elongate delivery catheter 232, where the sheath 250 can be moved longitudinally (e.g., slide) relative to the elongate delivery catheter 232 to allow the valve 200 to radially expand from its delivery state to its deployed state. In some embodiments, moving the retractable sheath 250 relative the delivery catheter 232 can be accomplished by pulling a proximal end 256 of the sheath 250 relative a proximal end 258 of the delivery catheter 232.

As illustrated in FIGS. 2A and 2B, the valve 200 also illustrated an embodiment of the present disclosure in which the biodegradable adhesive can be used to hold the valve leaflet 204 at one or more discrete attachment points 254 to the valve frame 202. As illustrated, the portions of the peripheral edge of the valve leaflet can be releasably joined to the valve frame at attachment points spaced equidistant from a longitudinally axis 260 of the valve frame.

In the compressed state, as illustrated in FIGS. 2A and 2B, attaching the valve leaflet 204 at the one or more discrete attachment points 254 to the valve frame 202 allows at least a portion of the commissure 206 of the valve leaflet 204 to gather toward the longitudinal axis 260 when the valve frame 202 is in a radially compressed state around either the expandable balloon 238 or compressed between the retractable sheath 250 and the elongate catheter 232.

In additional embodiment, the system can include both an expandable balloon positioned around at least a portion of the elongate delivery catheter and a retractable sheath. The valve frame can be at least partially self-expanding (or completely self-expanding), where retracting the sheath allows the valve to expand from its delivery state towards its deployed state. The expandable balloon can then be used to fully deploy, secure, and/or more fully seat the valve frame at the desired implant location.

Each of the delivery catheter 232 and/or the retractable sheath 250 can be formed of a number of materials. Materials include polymers, such as PVC, PE, POC, PET, polyamide, mixtures, and block co-polymers thereof. In addition, each of the delivery catheter 232 and/or the retractable sheath 250 can have a wall thickness and an inner diameter sufficient to allow the structures to slide longitudinally relative each other, as described herein, and to maintain the valve 200 in a delivery state, as discussed herein.

In an additional embodiment, the valve 200 of the present disclosure can include anchoring members attached to the valve frame or frame members. Anchoring members can include barbs, hooks, etc.

For the various embodiments, the valve of the present disclosure may be used with a patient that has been diagnosed with certain forms of heart failure, such as those having an essentially normal ejection fraction, but displaying signs and symptoms of heart failure. For example, in dealing with left ventricular (LV) diastolic dysfunction, improving left atrial (LA) systole can aid in the filling of a stiff LV (although not completely due to retrograde blood flow back into the pulmonary venous circulation). The valve of the present disclosure may help to improve the LA systolic contribution to LV diastolic filling when implanted at the junction where the pulmonary veins and the LA meet. Potentially, these valves will help improve the work done by the LA systole in moving a much greater percentage of blood forward into the LV during diastole.

In addition, positioning the system having the valve as discussed herein includes introducing the system into the cardiovascular system of the patient using minimally invasive percutaneous, transluminal techniques. For example, a guidewire can be positioned within the cardiovascular system of a patient that includes the predetermined location. The system of the present disclosure, including the valve as described herein, can be positioned over the guidewire and the system advanced so as to position the valve at or adjacent the predetermined location. In one embodiment, radiopaque markers on the catheter and/or the valve, as described herein, can be used to help locate and position the valve.

The valve can be deployed from the system at the predetermined location in any number of ways, as described herein. In one embodiment, valve of the present disclosure can be deployed and placed in any number of cardiovascular locations. For example, valve can be deployed and placed within an artery and/or vein (e.g., a pulmonary vein) of a patient. In one embodiment, arteries and/or veins of a patient include those of the peripheral vasculature and/or the cardiac vasculature. For example, delivery of one or more of the valves of the present disclosure to the pulmonary veins can be accomplished through transseptal puncture from the right atria into the left atria. In addition, embodiments of the valve have the potential to be used in a number of different vessels (e.g., urinary and/or lymph) where more stringent control over fluid movement is desired. Other locations are also possible.

Delivery of the valve can be accomplished through a number of different implant techniques. For example, the valve of the present disclosure can be implanted through the use of percutaneous delivery techniques, where the valve can be positioned at a predetermined location with the delivery catheter, as discussed herein. The valve can then be deployed from the delivery catheter at the predetermined location. The catheter can then be removed from the predetermined location.

The valve, once implanted, maintains its open luminal configuration in which the proximal end portion and the distal end portion of the valve leaflet are retained in a static relationship relative the valve frame after removal of the delivery catheter. In other words, the valve leaflet(s) are held in their "open" position through the use of the biodegradable adhesive, as discussed herein. Once implanted, the biodegradable adhesive is exposed to body fluids (e.g., blood) that cause its degradation and/or erosion to the point after the predetermined time where the valve leaflet(s) is released from its static relationship relative the valve frame.

During the predetermined time, however, the open luminal configuration allows for uncontrolled blood flow through the valve. Retaining the valve leaflets to create this open luminal configuration allows longitudinal shear stresses on the valve frame to be minimized during the predetermined time, as the valve leaflets are not opening and closing to provide for unidirectional flow through the valve. During this predetermined time, tissue in-growth can occur around the valve frame. This tissue in-growth can be promoted during the predetermined time through the use of coatings and/or surface treatments, such as those discussed herein.

While the present disclosure has been shown and described in detail above, it will be clear to the person skilled in the art that changes and modifications may be made without departing from the spirit and scope of the disclosure. As such, that which is set forth in the foregoing description and accompanying drawings is offered by way of illustration only and not as a limitation. The actual scope of the disclosure is intended to be defined by the following claims, along with the full range of equivalents to which such claims are entitled. In addition, one of ordinary skill in the art will appreciate upon reading and understanding this disclosure that other variations for the disclosure described herein can be included within the scope of the present disclosure.

In the foregoing Detailed Description, various features are grouped together in several embodiments for the purpose of streamlining the disclosure. This method of disclosure is not to be interpreted as reflecting an intention that the embodiments of the disclosure require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

The invention claimed is:

1. A valve, comprising:
   a valve frame;
   a valve leaflet coupled to the valve frame, where the valve leaflet has an open state and a closed state, and movement of the valve leaflet between the open state and the closed state provides for unidirectional flow of a liquid through the valve; and
   a biodegradable adhesive at one or more attachment points between the valve leaflet and the valve frame, the biodegradable adhesive holding the valve leaflet in the open state for a predetermined time of no less than one week after implantation into a lumen of a body.

2. The valve of claim 1, the valve further including a first treatment in regions other than the one or more attachment points, said treatment promoting tissue in-growth after implantation into a lumen of a body.

3. The valve of claim 2, the valve further including a second treatment at the one or more attachment points to prevent tissue in-growth at least for the predetermined time after implantation into a lumen of a body.

4. The valve of claim 1, the biological adhesive comprising a porous first portion for tissue in-growth after implantation into a lumen of a body.

5. The valve of claim 1, the biological adhesive having a layered structure.

6. The valve of claim 5, wherein said layered structure promotes tissue in-growth after implantation into a lumen of a body.

7. The valve of claim 6, the biodegradable adhesive being different types of biodegradable adhesive, the layered structure formed of the different types of biodegradable adhesives.

8. The valve of claim 1, where the valve frame includes a distal end and where the biodegradable adhesive holds the valve leaflet completely along the distal end of the valve frame.

9. The valve of claim 1, where the valve leaflet includes a commissure that can reversibly seal for unidirectional flow of a liquid through the valve after the predetermined time, further including allowing at least a portion of the commissure of the valve leaflet to gather toward the longitudinal axis when the valve frame is in a radially compressed state.

10. A system, comprising:
    an elongate delivery catheter; and
    a valve positioned at least partially over the elongate delivery catheter, where the valve includes:
       a valve frame;
       a valve leaflet coupled to the valve frame, where the valve leaflet has an open state and a closed state, and movement of the valve leaflet between the open state and the closed state provides for unidirectional flow of a liquid through the valve; and
       a biodegradable adhesive at one or more discrete attachment points between the valve leaflet and the valve frame, the biodegradable adhesive holding the valve leaflet in the open state for a predetermined time of no less than one week after implantation into a lumen of a body.

11. The system of claim 10, where the elongate delivery catheter includes an expandable balloon positioned around at least a portion of the elongate delivery catheter, and where the valve is positioned at least partially over the expandable balloon.

12. The system of claim 10, where the elongate delivery catheter includes a retractable sheath positioned over at least a portion of the valve, where the retractable sheath can be retracted to release the valve from the elongate delivery catheter.

13. The system of claim 10, where the valve frame includes a distal end and where the biodegradable adhesive holds the valve leaflet completely along the distal end of the valve frame.

14. The valve of claim 10, the valve further including a first treatment in regions of the valve other than the one or more attachment points, said treatment promoting tissue in-growth after implantation into a lumen of a body.

15. The valve of claim 14, the valve further including a second treatment at the one or more attachment points to prevent tissue in-growth at least for the predetermined time after implantation into a lumen of a body.

16. The valve of claim 10, the biological adhesive comprising a porous first portion for tissue in-growth after implantation into a lumen of a body.

17. The valve of claim 10, the biological adhesive having a layered structure.

18. The valve of claim 17, wherein said layered structure promotes tissue in-growth after implantation into a lumen of a body.

19. The valve of claim 18, the biodegradable adhesive being different types of biodegradable adhesive, the layered structure formed of the different types of biodegradable adhesives.

20. A valve, comprising:
   a valve frame;
   a valve leaflet coupled to the valve frame, where the valve leaflet has an open state and a closed state, and movement of the valve leaflet between the open state and the closed state provides for unidirectional flow of a liquid through the valve; and
   a biodegradable adhesive at one or more attachment points between the valve leaflet and the valve frame, the biological adhesive comprising a porous first portion for tissue in-growth after implantation into a lumen of a body, the biodegradable adhesive holding the valve leaflet in the open state for a predetermined time of no less than one week after implantation into a lumen of a body.

* * * * *